(12) United States Patent
Ho

(10) Patent No.: US 8,029,281 B2
(45) Date of Patent: Oct. 4, 2011

(54) SEPARATING RING

(76) Inventor: Phillip Phung-I Ho, Santa Barbara, CA (US)

( * ) Notice: Subject to any disclaimer, the term of this patent is extended or adjusted under 35 U.S.C. 154(b) by 316 days.

(21) Appl. No.: 12/120,088

(22) Filed: May 13, 2008

(65) Prior Publication Data

US 2009/0286200 A1 Nov. 19, 2009

(51) Int. Cl.
*A61C 3/00* (2006.01)
(52) U.S. Cl. .......................................................... 433/148
(58) Field of Classification Search ............... 433/39, 433/139, 140, 153, 155, 148, 149
See application file for complete search history.

(56) References Cited

U.S. PATENT DOCUMENTS

| | | | | |
|---|---|---|---|---|
| 388,620 A * | 8/1888 | Booth | ............................. | 433/39 |
| 427,338 A * | 5/1890 | Marshall | ....................... | 433/149 |
| 474,132 A * | 5/1892 | Ivory | ............................. | 433/158 |
| 486,112 A * | 11/1892 | Kuns | ............................. | 433/149 |
| 641,672 A * | 1/1900 | Brigham | ....................... | 433/139 |
| 5,607,302 A * | 3/1997 | Garrison et al. | ................ | 433/39 |
| 6,206,697 B1 * | 3/2001 | Hugo | ............................. | 433/155 |
| 6,293,796 B1 * | 9/2001 | Trom et al. | .................... | 433/155 |
| 6,325,625 B1 * | 12/2001 | Meyer | ............................. | 433/139 |
| 6,336,810 B1 * | 1/2002 | Bertoletti | ......................... | 433/39 |
| 6,589,053 B2 * | 7/2003 | Bills | ............................. | 433/139 |
| 6,666,683 B2 * | 12/2003 | Mungcal | ....................... | 433/149 |
| 2003/0129562 A1 * | 7/2003 | Mungcal | ....................... | 433/149 |
| 2003/0148245 A1 * | 8/2003 | Anderson | ....................... | 433/148 |
| 2005/0118554 A1 * | 6/2005 | Kilcher et al. | ................ | 433/141 |
| 2005/0147941 A1 * | 7/2005 | McDonald | .................... | 433/153 |

* cited by examiner

*Primary Examiner* — Todd Manahan
*Assistant Examiner* — Michael R Ballinger
(74) *Attorney, Agent, or Firm* — Hershkovitz & Associates, LLC; Abraham Hershkovitz

(57) ABSTRACT

A separating ring having a body being a resilient bent open ring and having two bent side bars having distal ends and wedge legs formed respectively on the distal ends, the wedge legs being spearheaded and fit easily between adjacent teeth to allow dental operations to be carried out easily and without the need for wedges.

8 Claims, 6 Drawing Sheets

SEPARATING RING

BACKGROUND OF THE INVENTION

1. Field of the Invention

The present invention relates to an integrated separating ring for separating adjacent teeth.

2. Description of the Prior Art

With reference to FIGS. 6 and 7, a conventional separating ring (91) is a resilient open ring used to separate adjacent teeth and comprises two ends having two perpendicular extending legs (911) formed parallelly with each other. The separating ring (91) is implemented with a matrix (92) and a wedge (93). The wedge (93) is carefully selected to ensure a correct size.

In dental surgery such as a dental restoration, a decayed tooth (81) having a hole (811) to be clinically treated and an outer surface having at least one adjacent surface is isolated from at least one adjacent tooth (82). A conventional method for separating the adjacent tooth (82) from the decayed tooth (81) comprises inserting the matrix (92) between the adjacent surface of the decayed tooth (81), mounting the legs (911) of the separating ring (91) to hold the matrix (92) in position and inserting the wedge (93) between the decayed tooth (81) and the adjacent tooth (82). To insert, the separating ring (91) is forced open with a pair of forceps then mounted between the adjacent tooth (82) and the matrix (92). Because the ring (91) is resilient, the ring forces the legs (911) together. The legs (911) being forced together firmly press the matrix (92) to the decayed tooth (81), thereby making tight contact of the matrix (92) with the decay tooth (81) possible.

A restorative material such as a dental composite is then used to fill the hole (811) of the decayed tooth (81) and solidifies in the hole (811) within the matrix (92). After removing the ring (91) and furnishing the outer surface of the decayed tooth (81) with dental composite, the decayed tooth (81) is restored.

However, keeping the ring (91) open requires a considerable force and inserting the legs (911) between the adjacent tooth (82) and the matrix (92) requires great skill and is complicated by keeping the ring open (91), which may lead to placement errors and increase time of the dental surgery, especially important when the dental surgery must be completed within a limited time.

The dental surgery may also be complicated by wedge (93) choosing, since a correct width of wedge must be judged, if the wedge (93) is too small, the wedge (93) will not hold the matrix (92) tightly against the decayed tooth (81) during the filling procedure. If the wedge (93) is too big, the wedge (93) will deform the shape of the filled decayed tooth (81) and may cause food traps.

Furthermore, according to disciplinary requirements in dentistry, a neat, clean and well-organized work area is indispensable for a dentist. However, storing and managing numerous wedges (93) of various sizes becomes a burden in maintaining a correct work area.

To overcome the shortcomings, the present invention provides a separating ring and a method for dental restoration to mitigate or obviate the aforementioned problems, especially problems regarding the need for using wedges.

SUMMARY OF THE INVENTION

The objective of the invention is to provide an integrated separating ring.

The separating ring in accordance with the present invention has a resilient body being a bent open ring and having two bent side bars and two wedge legs being of flat-spearheaded shape. The bent side bars have distal ends and provide a resilient force when separated. The wedge legs are formed respectively on and protrude transversely from the distal ends of the bent side bars to allow the wedge legs to fit easily between adjacent teeth. Because the wedge legs are of flat-spearheaded shape, they easily fit between two adjacent teeth and make dental procedures including composite filling restorations easier to carry out.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
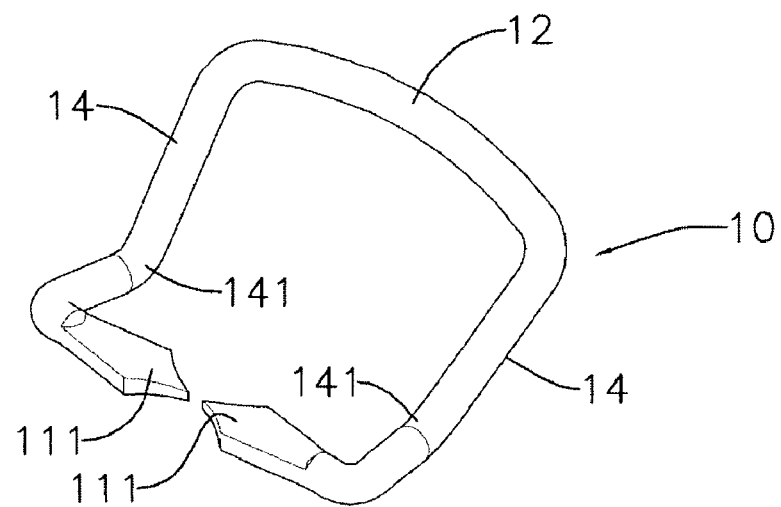
FIG. 1 is a perspective view of a separating ring in accordance with the present invention.

With reference to FIG. 1, a separating ring in accordance with the present invention is used to separating a decayed tooth (81) having an approximal surface from at least one adjacent tooth (82) and comprises a body (10) being a resilient open ring. The body (10) is mounted between the decayed tooth (81) and the adjacent tooth (82) and comprises a rear bar (12), two bent side bars (14) and two wedge legs (111). The body (10) may be metal or metal alloys such as but not limited to titanium and its alloys and steel and its alloys.

The rear bar (12) may be wider than the adjacent tooth (82), may be straight or curved and has two ends. The bent side bars (14) are formed on and protrude respectively from ends of the rear bar (12). Each of the bent side bars (14) has a distal end and a proximal end. The proximal end is connected to the rear bar (12). The proximal ends of the bent side bars (14) may be disposed wider than the distal ends of the bent side bars so that when the body (10) is forced open during surgery and then mounted between the decayed tooth (81) and the adjacent tooth (82), the distal ends of the bent side bars (14) will be pressed together with greater resilient force.

Figure 4:
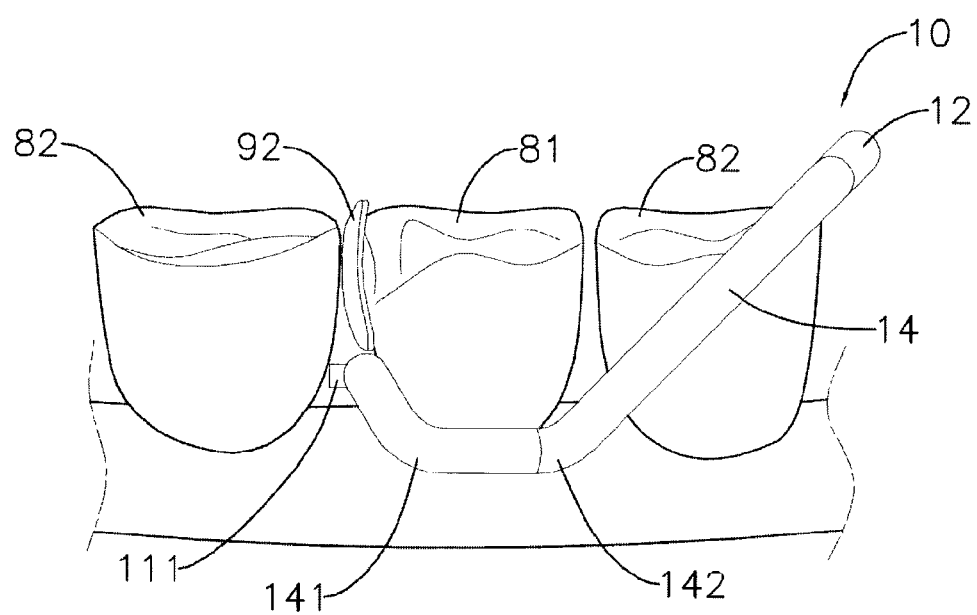
FIG. 4 is a side view of a second embodiment of a separating ring in accordance with the present invention.

With further reference to FIG. 4, each of the bent side bars (14) has at least one optional bending site (141, 142) being bent at an obtuse angle in the same orientation with the bending site (141) of the other bent side bar (14).

In another embodiment of the body, each of the bent side bars forms a gradual curve of the same shape and orientation with the other bent side bar.

Figure 5:
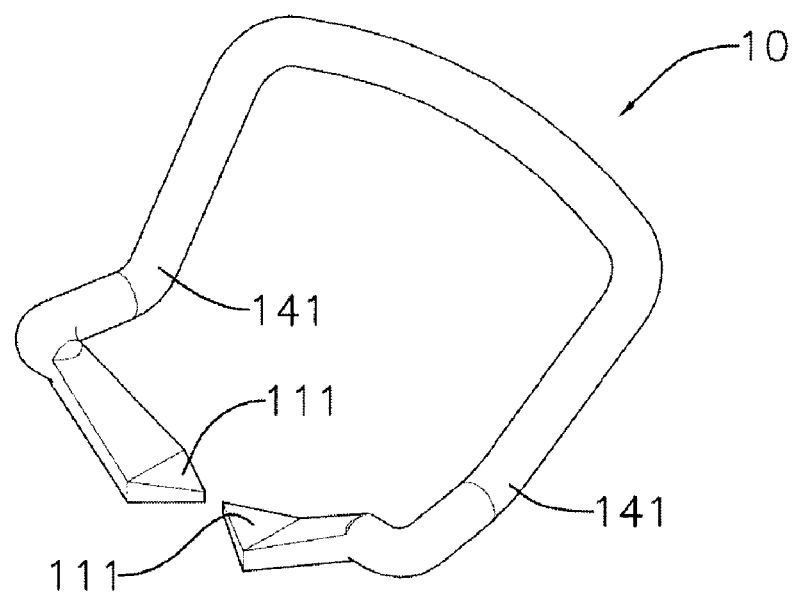
FIG. 5 is a perspective view of a third embodiment of a separating ring in accordance with the present invention.
Figure 6:
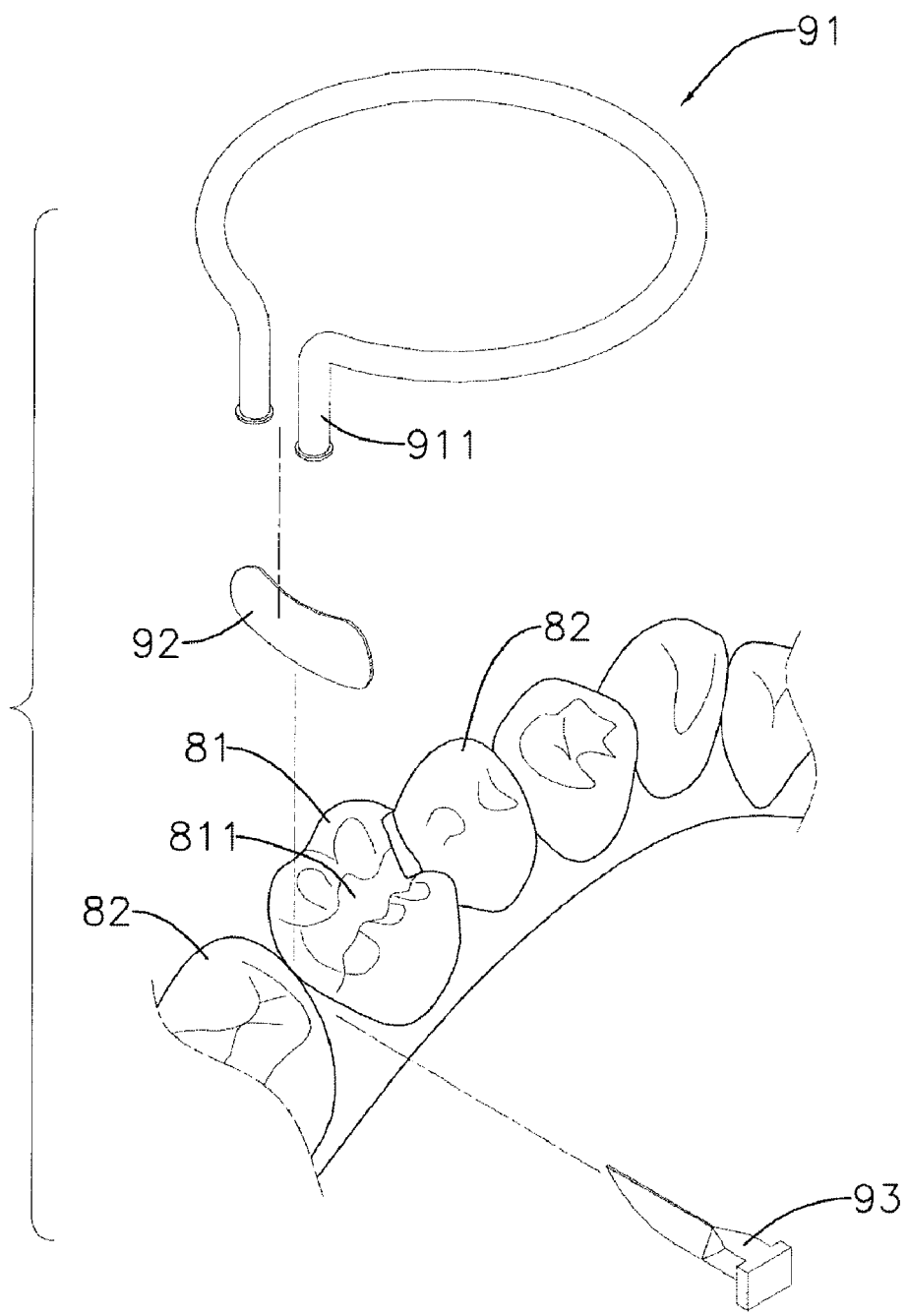
FIG. 6 is an operational view of a conventional separating ring in accordance with the prior art.
Figure 7:
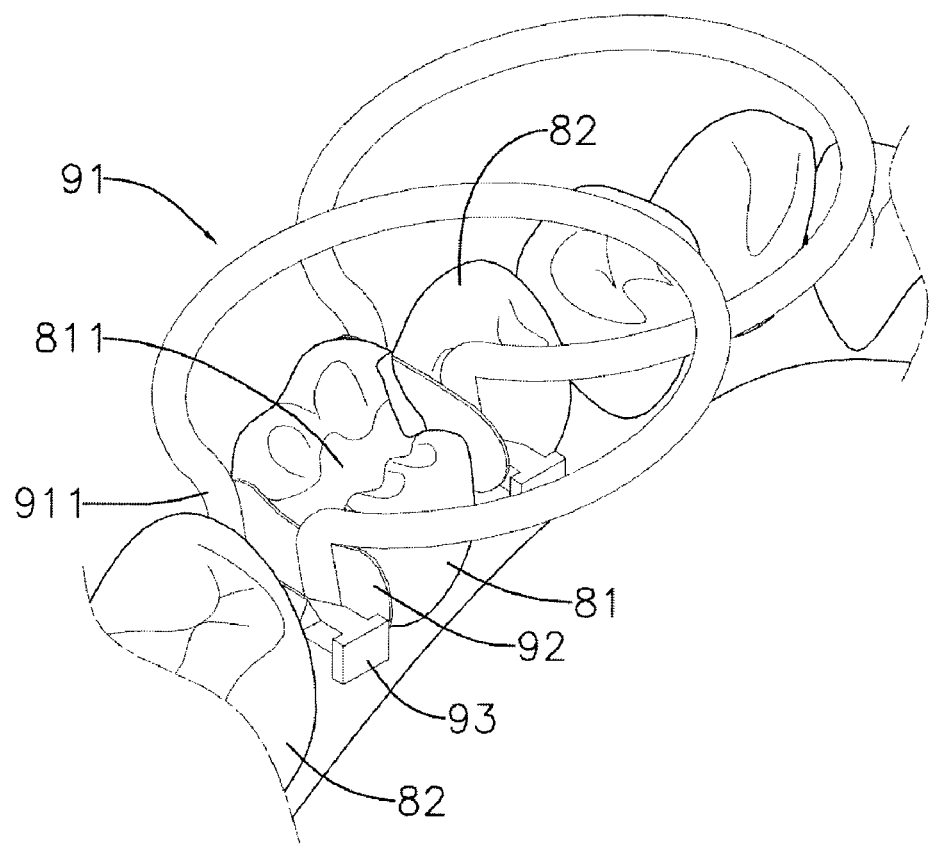
FIG. 7 is a perspective view of the conventional separating rings in FIG. 6 being mounted between teeth with matrices and wedges.

With reference to FIG. 5, the two wedge legs (111) are respectively formed on and protrude transversely from the distal ends of the bent side bars (14) and point at each other. Each wedge leg (111) may be flat, further bended or gingivally curved and is of flat-spearhead shape to form a point.

The body (10) is forced open so the points of the wedge legs (111) can be positioned on either side of the gap between the decayed tooth (81) and the adjacent tooth (82). The flat-spearheaded shapes of the wedge legs (111) help guide the wedge legs (111) into the gap to allow easy installation. The wedge legs (111) are driven by resilience of the body (10) into the gap to separate the decayed tooth (81) and the adjacent tooth (82). The wedge legs (111) are placed adjacent to the gum, and, on deeper restorations, even act to displace the gum apically.

Figure 2:
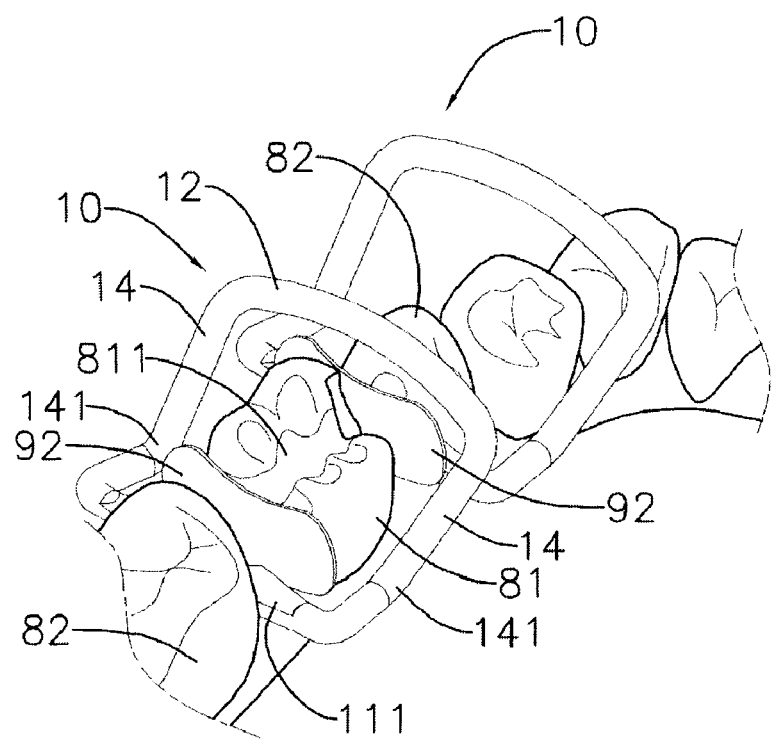
FIG. 2 is an operational perspective view of the separating ring in FIG. 1 mounted between teeth with a matrix.
Figure 3:
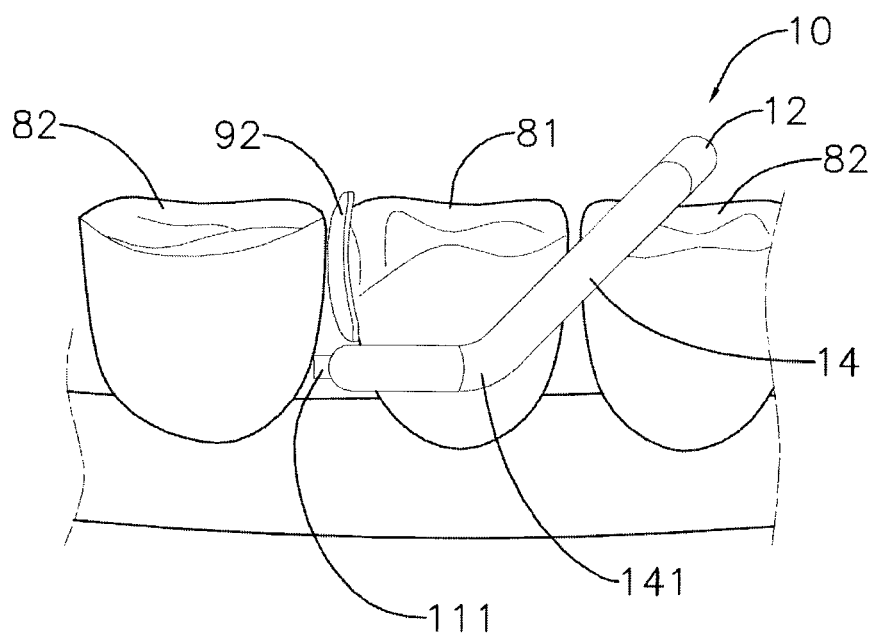
FIG. 3 is a side view of the separating ring and the matrix in FIG. 2.

With reference to FIGS. 2 and 3, the rear bar (12) is positioned above a crown of the adjacent tooth (82), and the bent side bars (14) are respectively positioned beside the lingual surface and the buccal surface of the decayed tooth (81). The gum portion of the bent side bars (14) may be disposed adjacent to the gums.

After inserting a matrix (92) against the decayed tooth (81), the body (10) of the separating ring is then mounted between the matrix (92) and the adjacent tooth (82).

Even though numerous characteristics and advantages of the present invention have been set forth in the foregoing description, together with details of the structure and features of the invention, the disclosure is illustrative only. Changes may be made in the details, especially in matters of shape, size, angles, extra bends, and arrangement of parts within the principles of the invention to the full extent indicated by the broad general meaning of the terms in which the appended claims are expressed.

What is claimed is:

1. An integrated separating ring comprising:
   a body being a resilient open ring and comprising a rear bar having two ends;
   two first side bars each having a proximal and distal ends, the proximal ends attached respectively to the ends of the rear bar, such that the rear bar and the first side bars lie substantially in a first plane;
   two second side bars attached to the distal ends of the first side bars and extending in a second plane disposed at an angle to the first plane; and
   two wedge legs being respectively formed on and protruding transversely from the second side bars and pointing inwardly toward each other, each wedge leg comprising a first planar section and a second planar section, the first planar sections being disposed at an angle with respect to the second plane and extending away from the rear bar and the second planar section being disposed at an angle with respect to the first planar section and terminating in a point.

2. The integrated separating ring as claimed in claim 1, wherein the angle to the first plane is an obtuse angle.

3. The integrated separating ring as claimed in claim 2, wherein the body is metal alloys, the rear bar is curved, and the proximal ends of the first side bars are disposed wider than the distal ends of the first side bars.

4. The integrated separating ring as claimed in claim 1, wherein the body is metal or metal alloys.

5. The integrated separating ring as claimed in claim 4, wherein the body is titanium, titanium alloys, steel or steel alloys.

6. The integrated separating ring as claimed in claim 1, wherein the rear bar is curved.

7. The integrated separating ring as claimed in claim 1, wherein the proximal ends of the first side bars are disposed wider than the distal ends of the first side bars.

8. The integrated separating ring as claimed in claim 1, wherein the body is metal alloys, the rear bar is curved, and the proximal ends of the first side bars are disposed wider than the distal ends of the first side bars.

\* \* \* \* \*